United States Patent
De Pater

(10) Patent No.: US 8,273,739 B2
(45) Date of Patent: Sep. 25, 2012

(54) METHOD FOR THE PURIFICATION OF MYCOPHENOLATE MOFETIL

(75) Inventor: Robertus Mattheus De Pater, Delft (NL)

(73) Assignee: DSM Sinochem Pharmaceuticals Netherlands B.V., Delft (NL)

( * ) Notice: Subject to any disclaimer, the term of this patent is extended or adjusted under 35 U.S.C. 154(b) by 297 days.

(21) Appl. No.: 12/666,846

(22) PCT Filed: Jun. 24, 2008

(86) PCT No.: PCT/EP2008/058021
§ 371 (c)(1),
(2), (4) Date: Dec. 28, 2009

(87) PCT Pub. No.: WO2009/000834
PCT Pub. Date: Dec. 31, 2008

(65) Prior Publication Data
US 2010/0190785 A1 Jul. 29, 2010

(30) Foreign Application Priority Data
Jun. 27, 2007 (EP) .................................... 07111199

(51) Int. Cl.
*A61K 31/5377* (2006.01)
*C07D 413/12* (2006.01)

(52) U.S. Cl. ..................................... 514/233.5; 544/153
(58) Field of Classification Search .................... None
See application file for complete search history.

(56) References Cited

U.S. PATENT DOCUMENTS

| 4,753,935 A * | 6/1988 | Nelson et al. .............. 514/233.5 |
| 5,247,083 A | 9/1993 | Knox et al. |
| 2004/0167130 A1 | 8/2004 | Lee et al. |

FOREIGN PATENT DOCUMENTS

WO WO 02/100855 12/2002

OTHER PUBLICATIONS

International Search Report for PCT/EP2008/058021, mailed Dec. 2, 2008.

* cited by examiner

*Primary Examiner* — Jason M Nolan
*Assistant Examiner* — Michael Barker
(74) *Attorney, Agent, or Firm* — Nixon & Vanderhye P.C.

(57) ABSTRACT

The present invention provides a method for the preparation of mycophenolate mofetil wherein mycophenolic acid or an amine salt of mycophenolic acid is esterified with 2-morpholinoethanol, the resulting mixture is extracted into water at a pH-value between 1.0 and 3.0, and mycophenolate mofetil is back-extracted in a water-immiscible solvent at a pH-value between 3.0 and 5.0.

7 Claims, No Drawings

METHOD FOR THE PURIFICATION OF MYCOPHENOLATE MOFETIL

This application is the U.S. national phase of International Application No. PCT/EP2008/058021 filed 24 Jun. 2008 which designated the U.S. and claims priority to EP Application No. 07111199.1 filed 27 Jun. 2007, the entire contents of each of which are hereby incorporated by reference.

FIELD OF THE INVENTION

The present invention relates to a method for the purification of mycophenolate mofetil.

BACKGROUND OF THE INVENTION

Mycophenolic acid (MPA, also known as 6-(4-hydroxy-6-methoxy-7-methyl-3-oxo-5-phthalanyl)-4-methyl-4-hexenoic acid, 6-(1,3-dihydro-4-hydroxy-6-methoxy-7-methyl-3-oxo-5-isobenzofuranyl)-4-methyl-4-hexenoic acid, $C_{17}H_{20}O_6$, CAS 24280-93-1) is a compound with various advantageous properties. Next to antibiotic activity, MPA also displays antifungal, antiviral and antitumor properties and the compound has been used in the treatment of psoriasis and recently as immunosuppressant. The 2-morpholinoethyl ester of MPA, also known as mycophenolate mofetil (MPM, $C_{23}H_{31}NO_7$, CAS 128794-94-5), is a prodrug of MPA and has similar advantageous properties. The chemical structure of MPM is:

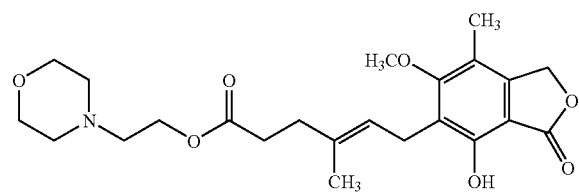

MPM can be prepared by esterification of MPA with 2-morpholinoethanol. In U.S. Pat. No. 4,753,935 an acid halide condensation route has been described. This is a two-step process requiring toxic reagents for forming the halide of MPA and/or of 2-morpholinoethanol. In EP 649,422 B1, an improved route was disclosed concerning refluxing MPA with 2-morpholinoethanol in an inert organic solvent capable of azeotropic removal of water, without the use of additional reagents. One of the major problems associated with the synthesis of MPM is the formation of unwanted impurities. One of those impurities is Impurity B ($C_{29}H_{42}N_2O_9$) which has the following chemical structure:

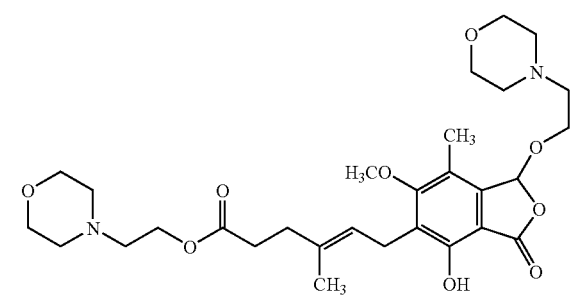

The origin of Impurity B is believed to reside in the production process leading to MPA, where a hydroxylated derivative of MPA (MPA-OH, $C_{17}H_{21}O_7$) is formed which is then converted to Impurity B during esterification with 2-morpholinoethanol, however also other hypotheses are feasible. The chemical structure of MPA-OH is:

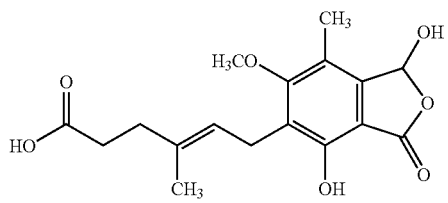

Regardless of the origin of Impurity B, synthetic and/or downstream processing methods towards the preparation of MPM with acceptable levels of Impurity B are highly desirable. According to the European Pharmacopoeia not more than 0.2% Impurity B may be present in MPM. Known approaches towards lowering the amount of Impurity B are well-known techniques such as recrystallization and/or chromatographic purification as for instance suggested in U.S. Pat. No. 5,247,083. However, such approaches result in significant losses of the desired product MPM and both are cumbersome and expensive, the last issue being particularly true for chromatographic purification. Hence, there is a need for an efficient and cheap method for lowering the amount of Impurity B in MPM.

DETAILED DESCRIPTION OF THE INVENTION

During esterification of MPA with 2-morpholinoethanol followed by isolation of the resulting MPM, in many cases the product contains too high a level of Impurity B. It was surprisingly found that the amount of Impurity B could be lowered significantly by a simple and hitherto unprecedented extraction procedure carried out during downstream processing of the esterification mixture.

In the first aspect of the invention MPA or an amine salt of MPA is esterified in a conversion with 2-morpholinoethanol. Preferably said esterification is carried out in a solvent, preferably at elevated temperatures. The solvent used for esterification of MPA can be a solvent such as benzene and substituted benzenes like ethyl benzene, meta-xylene, ortho-xylene, para-xylene and toluene, chloroform, methylene chloride, ethers such as dialkyl ethers like dibutyl ether and diisopropyl ether, ketones such as acetone, cyclohexanone, cyclopentanone, dipropyl ketone, methylisobutyl ketone, methylpropyl ketone and mixtures of these solvents. Preferred solvents are xylene, dibutyl ether and cyclohexanone. Preferably the esterification is carried out under azeotropic separation of water and under use of an excess of 2-morpholinoethanol, for instance 1.00 to 20 molar equivalents, preferably 1.01 to 10 molar equivalents, more preferably 1.02 to 5 molar equivalents, most preferably 1.03 to 3 molar equivalents, still most preferably 1.04 to 2 molar equivalents. Although the present invention is most suitably carried out under refluxing conditions, also esterification reactions carried out at lower temperatures than the boiling point can be further optimized by the presence of the chelating agent. The advantages of esterification at a temperature below the boiling point are that equipment for condensing solvent vapors and returning these condensed vapors are no longer required and the energy input required to reach and maintain the boiling point, which normally is substantial, can be circumvented. Furthermore, formation of unwanted by-products generally is lower at lower reaction temperatures.

The method of the present invention for the preparation of mycophenolate mofetil comprises the steps of:
(a) esterification of mycophenolic acid or an amine salt of mycophenolic acid with 2-morpholinoethanol;
(b) contacting the mixture obtained in step (a) with water at a pH-value between 1.0 and 3.0;
(c) separating the aqueous phase from the mixture obtained in step (b);
(d) contacting the aqueous phase obtained in step (c) with a water-immiscible solvent;
(e) separating the non-aqueous phase from the mixture obtained in step (d), characterized in that step (d) is carried out at a pH-value between 3.0 and 5.0.

In the context of the present invention the term "water-immiscible solvent" refers to a solvent which, when mixed with water, forms a two-phase system and which dissolves in water to an extent that the resulting aqueous phase contains less than 10% by weight of the solvent, preferably less than 1% by weight of the solvent, more preferably less than 0.5% by weight of the solvent. While one can imagine certain inorganic liquids such as silicone fluids and halocarbon liquids which meet the definition and which are included in the definition of "water-immiscible solvents", the far more common and thus preferred "water-immiscible solvents" are organic solvents, especially solvents comprising hydrocarbons and/or halohydrocarbons. Representative suitable water-immiscible solvents include $C_4$ to $C_{14}$ branched, cyclic, and straight chain saturated and unsaturated aliphatic hydrocarbons; $C_6$ to $C_{12}$ alkaryl hydrocarbons; and halohydrocarbons containing up to about 4 halogen atoms, especially chlorine, and from 1 to about 8 carbon atoms. It is also very suitable to employ mixtures of these materials or distillation fractions composed primarily of these materials. Thus, representative water-immiscible solvents include suitable freons, carbon tetrachloride, chloroform, methylene chloride, trichloroethylene, dichloropropane, and similar halohydrocarbons, n-pentane, n-hexane, cyclohexane, 2-methylpentane, hex-1-ene, benzene, n-heptane, methylcyclohexane, cyclopentanone, cyclohexanone, branched heptanes and heptenes, toluene, the normal and branched octanes and octenes, the xylenes, ethylbenzene, n-nonane and the branched nonanes, the various decanes, the dodecanes and like hydrocarbons, $C_6$-$C_7$, $C_6$-$C_8$ and $C_7$-$C_8$ naphtha fractions, mixed xylene-ethylbenzene fractions and the like, $C_4$ to $C_{14}$ branched, cyclic, and straight chain alcohols, esters and ketones. Preferred water-immiscible solvents are the $C_6$ to $C_8$ hydrocarbons including aliphatics like n-hexane, cyclohexane, n-heptane and n-octane and fractions composed in substantial part by these aliphatics and the aromatics such as benzene, toluene, ethylbenzene, xylenes and fractions composed in substantial part by these aromatics.

The pH-value used in step (b) can be further optimized to combine minimal loss of product resulting from degradation with maximal extraction yield. It has been found that the pH-value should be between 1.0 and 3.0, preferably between 1.5 and 2.7, more preferably between 1.8 and 2.4 and most preferably between 2.0 and 2.2.

The pH-value used in step (d) can be further optimized to combine maximal reduction of Impurity B with maximal extraction yield of the desired MPM. It has been found that the pH-value should be between 3.0 and 5.0, preferably between 3.75 and 4.75, more preferably between 4.0 and 4.5 and most preferably between 4.2 and 4.3. It has been found that at the pH-ranges mentioned above there is an unexpected difference in extraction behaviour between MPM and Impurity B where the former appears to dissolve to a very large extent in the organic phase whereas the latter dissolves to a large extent in the aqueous phase.

In US 2004/167130 it was suggested to add acid to crude mycophenolate mofetil to form an acid salt of mycophenolate mofetil to be soluble in the aqueous solution. However, US 2004/167130 does not specify exactly which pH values are required and the document neither indicates any effect on the presence, absence or diminishing of impurities. The specific pH regime described above surprisingly influences the amount of Impurity B present in the final product.

In a first embodiment of the present invention MPA is used in the form of a salt. Suitable salts are amines and alkali metal salts. In case of alkali metal salts, also an acid should be present in a molar amount that is at least equal to that of the molar amount of the MPA alkali metal salt. In case of amine salts, addition of acid is not mandatory, although acid can also be added in order to decrease conversion times and/or increase yields. Examples of suitable amine salts of MPA are, but are not limited to, salts from amines such as tert-butylamine, cyclohexylamine, dibenzylamine, N,N-diisopropylethylamine, N,N-dimethylcyclohexylamine, N,N-dimethylisopropylamine, N-methyl-piperidine, morpholine, tert-octylamine, piperidine, iso-propylamine, N,N,N',N'-tetramethylbutylenediamine, N,N,N',N'-tetramethylethylenediamine, tributylamine, triethyl-amine and tripropylamine. Suitable alkali metal salts of MPA are salts from lithium and potassium, preferably from sodium.

In a second embodiment of the present invention, esterification of MPA or an MPA salt can be positively influenced (i.e. reduction of reaction time, increase of maximum conversion) by the addition of substances that are capable of absorbing water. These substances can be present in the mixture of MPA, solvent and 2-morpholinoethanol. However, these substances may also be present in the vapor phase of said mixture; despite the fact that the present invention deals with a method for esterification in non-boiling mixtures, a vapor phase nevertheless is usually present above such non-boiling mixtures. Substances that are capable of absorbing water are for instance salts of alkali and earth alkali metals and usually these salts are carbonates, halides or sulfates. Suitable examples are $CaCl_2$, $CaSO_4$, $K_2CO_3$, $K_2SO_4$, $MgSO_4$, $Na_2CO_3$, $Na_2SO_4$ and the like. Preferred other substances are molecular sieves, preferably those with pore sizes ranging from 0.1-0.6 nm, more preferably ranging from 0.2-0.5 nm, most preferably ranging from 0.3-0.4 nm.

In a second aspect of the invention, MPM is obtained according to the method of the first aspect. Said MPM contains less than 0.05% by weight of Impurity B, preferably between 0.001% and 0.03% by weight of Impurity B, more preferably between 0.002% and 0.02% by weight of Impurity B, most preferably between 0.005% and 0.01% by weight of Impurity B.

In a third aspect of the present invention, MPM obtainable according to the first aspect can be used in pharmaceutical compositions, for instance in antifungal, antiviral and/or anti-tumor compositions, but also in compositions useful in the treatment of psoriasis and as immunosuppressant. Accordingly, said pharmaceutical compositions have the advantage that the amounts of Impurity B present in said compositions are at hitherto unprecedented low levels.

EXAMPLES

General Methods

HPLC analysis was performed on a Waters HPLC\MS system (Alliance HT 2795 separation module; Diode array detector, model 996) with the following specifics:

Column: Waters Sunfire C18, 150×4.6 mm, 3.5 μm
Column temp: 40° C.
Flow rate: 1.0 ml/min
UV-detection 251 nm (and 214 nm for the determination of xylene)
Injection volume: 5 μl (use fixed loop)
Mobile phase A: Sörensen buffer/water (30/70)
Mobile phase B: Sörensen buffer/ACN (30/70)

| Gradient: | T = 0 min. | 50% B |
|---|---|---|
| | T = 12 min. | 70% B |
| | T = 16 min | 100% B |
| | T = 21.4 min | 100% B |
| | T = 21.5 min | 50% B |
| | T = 28 min | 50% B |

The chemicals are water (Milli-Q purified or HPLC grade), acetonitrile (ACN, gradient grade, Merck 1.00030), $KH_2PO_4$ (p.a., Merck 1.04873), $Na_2HPO_4 \cdot 2H_2O$ (p.a., Merck 1.06580).

Mobile Phases:
Phosphate solution A: 3.026 g of $KH_2PO_4$ was dissolved in 1 L MilliQ water.
Phosphate solution B: 3.9587 g of $Na_2HPO_4 \cdot 2H_2O$ was dissolved in 1 L MilliQ water.
Sörensen buffer (0.022 M, pH 6.4): 700 mL phosphate solution A was mixed with 300 mL phosphate solution B.

References, Standards and Controls:
Standard: PH Eur reference for peak identification CRS (contains mycophenolate mofetil with impurities A, B, D, E, F, G and H).

Example 1

Conversion of MPA-Triethylamine Salt (MPA-TEA) Into MPM

MPA-TEA (15.0 g; 73.5% MPA; 1.1% MPA-OH; 34.5 mmol MPA) and 2-morpholino-ethanol (2.25 ml; 18.3 mmol) were suspended in xylene (60 ml). The mixture was heated to 120-125° C. A positive nitrogen flow was applied during the reaction. After 6 hours additional 2-morpholinoethanol (1.55 ml; 12.6 mmol) was added. After 22 hours another portion of 2-morpholinoethanol (0.7 ml; 5.7 mmol) was added (in total 4.5 ml 2-morpholinoethanol; 36.6 mmol). The reaction was followed by HPLC:

| Reaction time (h) | Molar excess 2-morpholinoethanol | Conversion to MPM (%) | Ratio Impurity B/MPM (w/w %) |
|---|---|---|---|
| 3 | 0.5 | 24.5 | 0.16 |
| 6 | 0.5 | 39.7 | 0.23 |
| 22 | 0.9 | 74.9 | 0.60 |
| 29 | 1.1 | 81.0 | 0.58 |
| 46.5 | 1.1 | 87.1 | 0.65 |
| 54 | 1.1 | 88.4 | 0.63 |
| 71 | 1.1 | 90.3 | 0.64 |

After the analytical sample at 71 h, the reaction mixture was cooled to 12±3° C. and the mixture thus obtained contained 91.4% (w %) MPM and 0.58% (w %) Impurity B.

Example 2

Purification of MPM by Extraction at Different pH Values

The reaction mixture obtained in Example 1 (60 ml) was diluted with water (60 ml). Under stirring the pH was adjusted to 2 with 6N $H_2SO_4$ at 12±3° C. The phases were separated. The aqueous phase was extracted three times with EtOAc (40 ml) at pH 2.2 at 12±3° C. in order to remove unconverted MPA. The aqueous phase was divided into six portions of 20 ml. To each portion EtOAc (40 ml) was added and the pH of the six mixtures was adjusted to 3.5, 3.75, 4.0, 4.25, 4.5 and 5.0, respectively using 4N NaOH at room temperature. The phases were separated, giving EtOAc phases 1 and water phases 1; these phases were analyzed by HPLC.

All EtOAc phases 1 were washed with 20 ml water at the same pH as the fore-going extraction (3.5, 3.75, 4.0, 4.25, 4.5 and 5.0, respectively) at room temperature. The phases were separated giving EtOAc phases 2 and water phases 2; also these phases were analyzed by HPLC.

The results are as follows:

Extraction at pH 3.5

| Phase | MPM (g/l) | Impurity B (g/l) | Yield MPM (%) | Impurity B/MPM (%) |
|---|---|---|---|---|
| EtOAc 1 | 22.79 | 0 | 54.0 | 0 |
| Water 1 | 46.31 | 0.67 | 46.0 | 1.45 |
| EtOAc 2 | 19.61 | 0 | 79.4 | 0 |
| Water 2 | 8.86 | 0.0145 | 20.6 | 0.16 |

At pH 3.5 Impurity B is not extracted into EtOAc.
Yield MPM over first extraction is 54%.
Yield loss over washing of the EtOAc-extract is 21%.
MPM-yield over extraction and wash-step is 43%.

Extraction at pH 3.75

| Phase | MPM (g/l) | Impurity B (g/l) | Yield MPM (%) | Impurity B/MPM (%) |
|---|---|---|---|---|
| EtOAc 1 | 35.69 | 0 | 84.2 | 0 |
| Water 1 | 16.39 | 0.67 | 15.8 | 4.1 |
| EtOAc 2 | 34.03 | 0 | 87.5 | 0 |
| Water 2 | 8.42 | 0.0218 | 12.5 | 0.26 |

At pH 3.75 Impurity B is not extracted into EtOAc.
Yield MPM over first extraction is 84%.
Yield loss over washing of the EtOAc-extract is 13%.
MPM-yield over extraction and wash-step is 74%.

Extraction at pH 4.0

| Phase | MPM (g/l) | Impurity B (g/l) | Yield MPM (%) | Impurity B/MPM (%) |
|---|---|---|---|---|
| EtOAc 1 | 40.20 | 0.0213 | 94.4 | 0.05 |
| Water 1 | 5.87 | 0.66 | 5.6 | 11.24 |
| EtOAc 2 | 38.94 | 0 | 89.8 | 0 |
| Water 2 | 7.39 | 0.0313 | 10.2 | 0.42 |

At pH 4.0 Impurity B is almost not extracted into EtOAc.
The amount is below 0.1%.
Yield MPM over first extraction is 94%.
Yield loss over washing of the EtOAc-extract is 10%.
MPM-yield over extraction and wash-step is 85%.

Extraction at pH 4.25

| Phase | MPM (g/l) | Impurity B (g/l) | Yield MPM (%) | Impurity B/MPM (%) |
|---|---|---|---|---|
| EtOAc 1 | 39.79 | 0.035 | 97.5 | 0.09 |
| Water 1 | 2.53 | 0.55 | 2.5 | 21.7 |
| EtOAc 2 | 39.75 | 0 | 94.0 | 0 |
| Water 2 | 4.40 | 0.0835 | 6.0 | 1.9 |

After extraction at pH 4.25 0.1% of Impurity B is found in the first EtOAc-extract.
Yield MPM over first extraction is 98%.
Yield loss over washing of the EtOAc-extract is 6%.
MPM-yield over extraction and wash-step is 92%.

Extraction at pH 4.5

| Phase | MPM (g/l) | Impurity B (g/l) | Yield MPM (%) | Impurity B/MPM (%) |
|---|---|---|---|---|
| EtOAc 1 | 43.30 | 0.086 | 98.3 | 0.20 |
| Water 1 | 1.67 | 0.45 | 1.7 | 26.9 |
| EtOAc 2 | 44.46 | 0 | 96.0 | 0 |
| Water 2 | 3.22 | 0.158 | 4.0 | 4.9 |

After extraction at pH 4.5, 0.2% of Impurity B is in the first EtOAc-extract.
Yield MPM over first extraction: 98%.
Yield loss over washing of the EtOAc-extract: 4%.
Impurity B can be reduced to <0.1% by this step.
MPM-yield over extraction and wash-step is 94%.

Extraction at pH 5.0

| Phase | MPM (g/l) | Impurity B (g/l) | Yield MPM (%) | Impurity B/MPM (%) |
|---|---|---|---|---|
| EtOAc 1 | 41.54 | 0.225 | 99.3 | 0.54 |
| Water 1 | 0.77 | 0.121 | 0.7 | 15.7 |
| EtOAc 2 | 43.18 | 0.225 | 99.4 | 0.52 |
| Water 2 | 0.44 | 0.0438 | 0.6 | 9.9 |

After extraction at pH 5.0, 0.5% of Impurity B is found in the first EtOAc-extract.
Yield MPM over first extraction is 99%.
Yield loss over washing of the EtOAc-extract is 1%.
After this wash-step 0.5% Impurity B is found in the extract.
MPM-yield over extraction and wash-step is 99%.

Example 3

Isolation of MPM

The reaction mixture obtained in Example 1 (60 ml) was diluted with water (60 ml). Under stirring the pH was adjusted to 2 with 6N $H_2SO_4$ (4.7 ml) at 12±3° C. The phases were separated and the aqueous phase was extracted three times with EtOAc (3×40 ml) at pH 2.1 at 12±3° C. EtOAc (160 ml) was added to the water phase and the pH was adjusted to 4.25 with 4N NaOH (8.3 ml). The phases were separated and were analyzed by HPLC (water phase 1 and EtOAc phase 1). The EtOAc phase was washed with 80 ml water at pH 4.5 (pH adjustment with 20 µl 6N $H_2SO_4$). The phases were separated giving water phase 2 and EtOAc phase 2. Both phases were analyzed by HPLC. Water (80 ml) was added to EtOAc phase 2 and the pH was adjusted to 8.15 with 4N NaOH (~0.1 ml). The phases were separated and the EtOAc phase 3 was analyzed by HPLC as summarized in the Table below. Finally EtOAc phase 3 was washed with water at pH ~6.

ZetaCarbon powder R55SP from Cuno (0.75 g) was added and the mixture was stirred for 1 hour. The carbon was filtered off and washed with 50 ml EtOAc. The filtrate was evaporated under vacuum at 70° C. (bath temperature) and the residue was dissolved in 15 ml EtOAc and 75 ml 1-propanol at 50° C. Under stirring the mixture was gradually cooled to 0-5° C. (nucleation at 37-38° C.). The crystals were filtered off, washed with two cake-volumes 1-propanol of 0-5° C., and dried under vacuum at 40-45° C., yielding 11.08 g (yield 74.3%) MPM as white crystals containing 99.9% MPM and 0.006% Impurity B.

| Phase | MPM (g/l) | Impurity B (g/l) | Yield MPM (%) | Impurity B/MPM (w/w %) |
|---|---|---|---|---|
| EtOAc 1 | 63.0 | 48 | 97.4 | 0.08 |
| Water 1 | 3.87 | 680 | 2.6 | 17.6 |
| EtOAc 2 | 63.7 | 15 | 98.4 | 0.02 |
| Water 2 | 2.02 | 55 | 1.6 | 2.7 |
| EtOAc 3 | 66.3 | 21 | 99.4 | 0.03 |

The invention claimed is:

1. Method for the preparation of mycophenolate mofetil comprising the steps of:
   (a) esterification of mycophenolic acid or an amine salt of mycophenolic acid with 2-morpholinoethanol;
   (b) contacting the mixture obtained in step (a) with water at a pH-value between 1.0 and 3.0;
   (c) separating the aqueous phase from the mixture obtained in step (b);
   (d) contacting the aqueous phase obtained in step (c) with a water-immiscible solvent;
   (e) separating the non-aqueous phase from the mixture obtained in step (d), characterized in that step (d) is carried out at a pH-value between 3.0 and 5.0.

2. Method according to claim 1 wherein step (a) is carried out in a water-immiscible solvent.

3. Method according to claim 2 wherein step (a) is carried out under azeotropic removal of water.

4. Method according to claim 1 wherein step (d) is carried out at a pH-value between 3.5 and 4.5.

5. A composition comprising mycophenolate mofetil and between 0.002% (w/w) and 0.05% (w/w) of a compound of formula (1):

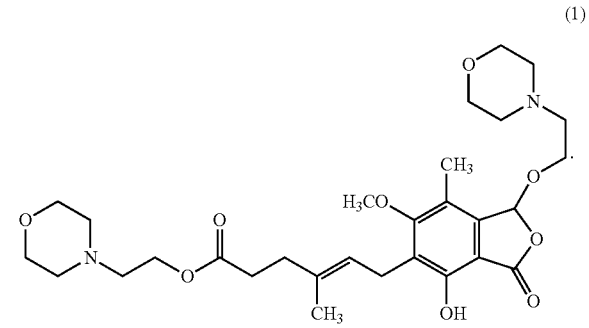

(1)

6. A pharmaceutical composition comprising mycophenolate mofetil and between 0.002% (w/w) and 0.05% (w/w) of a compound of formula (1):
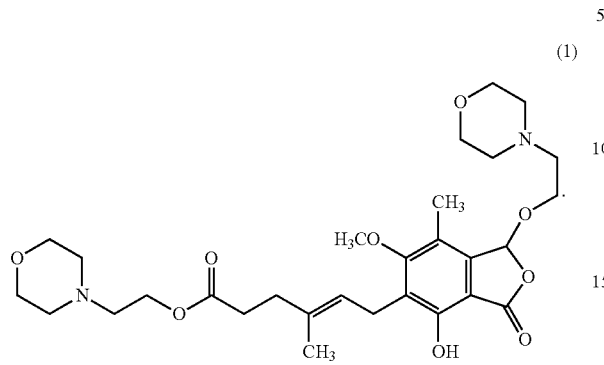
(1)
7. A medicament which comprises mycophenolate mofetil and between 0.002% (w/w) and 0.05% (w/w) of a compound of formula (1):
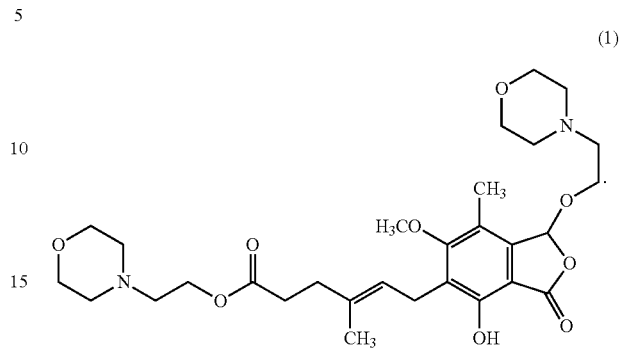
(1)
\* \* \* \* \*